US006268123B1

(12) United States Patent
Faff

(10) Patent No.: US 6,268,123 B1
(45) Date of Patent: *Jul. 31, 2001

(54) DIRECT AND BIOCHEMICALLY FUNCTIONAL DETECTION PROCESS OF RETROVIRUS IN BIOLOGICAL SAMPLES

(75) Inventor: Ortwin Faff, Unterschleissheim (DE)

(73) Assignee: Retro-Tech GmbH, Unterschleissheim (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/557,108

(22) PCT Filed: May 31, 1994

(86) PCT No.: PCT/DE94/00610

§ 371 Date: Feb. 28, 1996

§ 102(e) Date: Feb. 28, 1996

(87) PCT Pub. No.: WO94/28115

PCT Pub. Date: Dec. 8, 1994

(30) Foreign Application Priority Data

Jun. 1, 1993 (DE) .................................................. 43 18 229
May 9, 1994 (DE) .................................................. 44 16 300

(51) Int. Cl.[7] ...................................................... C12Q 1/70
(52) U.S. Cl. ................................... 435/5; 435/6; 435/7.1; 435/7.2; 435/7.5; 435/7.6; 435/7.8; 435/7.9; 435/7.92; 435/91.33; 435/961; 435/968; 435/974; 436/525; 436/526; 436/529; 436/531; 436/532; 436/534
(58) Field of Search ............................. 435/5, 7.1, 6, 7.2, 435/7.5, 7.6, 7.8, 7.9, 7.92, 91.31, 91.32, 91.33, 239, 961, 968, 974; 436/525, 526, 529, 531, 532, 534

(56) References Cited

U.S. PATENT DOCUMENTS 5,077,192 * 12/1991 Liang et al. ............................. 435/5

5,534,406 * 7/1996 Liang et al. ............................. 435/5

FOREIGN PATENT DOCUMENTS

93/07259 * 4/1993 (WO) .

OTHER PUBLICATIONS

Faff et al. "Retrovirus–Like Particles from the Human T47D Cell Line are Related to Mouse Mammary Tumour Virus and are of Human Endogenous Origin" *The Journal of General Virology*, vol. 73, part 5(May 1992), pp. 1087–1097.*

Eberle and Seibl, 1992 "A New Method For Measuring Reverse Transcriptase Activity By ELISA," *J. Virol. Meth.* 40:347–356.

Faff et al., 1989, "Microassay of Reverse Transcriptase In Microtiterplates," *Methods in Mol. and Cell. Biol.* 1:67–72.

Faff et al., 1993, "Large Scale Production And Purification Of Human Retrovirus–Like Particles Related To The Mouse Mammary Tumor Virus" *FEMS Microbiology Letters* 109:289–296.

Gallo, 1991, "Ein Krebsvirus Wird Entdeckt: Das Erste Menschliche Retrovirus," *Die Jagd Nach Dem Virus ed, S. Fischer*, pp. 144–165.

Henrard et al., 1992, "A Sensitive Viral Capture Assay For Detection Of Plasma Viremia In HIV–Infected Individuals," *AIDS Res. Hum. Retrovir.* 8:47–52.

Holodniy et al., 1991, "Detection And Quantification Of Human Immunodeficiency Virus RNA In Patient Serum By Use Of The Polymerase Chain Reaction," *J. Infect. Dis.* 163:862–866.

Kurth et al., 1993, "Entdeckung Von Viren Im Meschlichen Erbgut," *Spektrum der Wissenschaft* 9:15–17.

* cited by examiner

Primary Examiner—Jeffrey Stucker
(74) Attorney, Agent, or Firm—Pennie & Edmonds LLP

(57) ABSTRACT

The present invention relates to processes for the direct detection of biochemically functional retroviruses in biological samples. The processes of the invention are characterized by the structure-specific extraction of retrovirus particles and a subsequent analysis and detection of retrovirus-specific enzymatic reactions. The processes of the invention have broad application in the diagnosis of retroviral infection and virological research.

17 Claims, 1 Drawing Sheet

Figure 1:
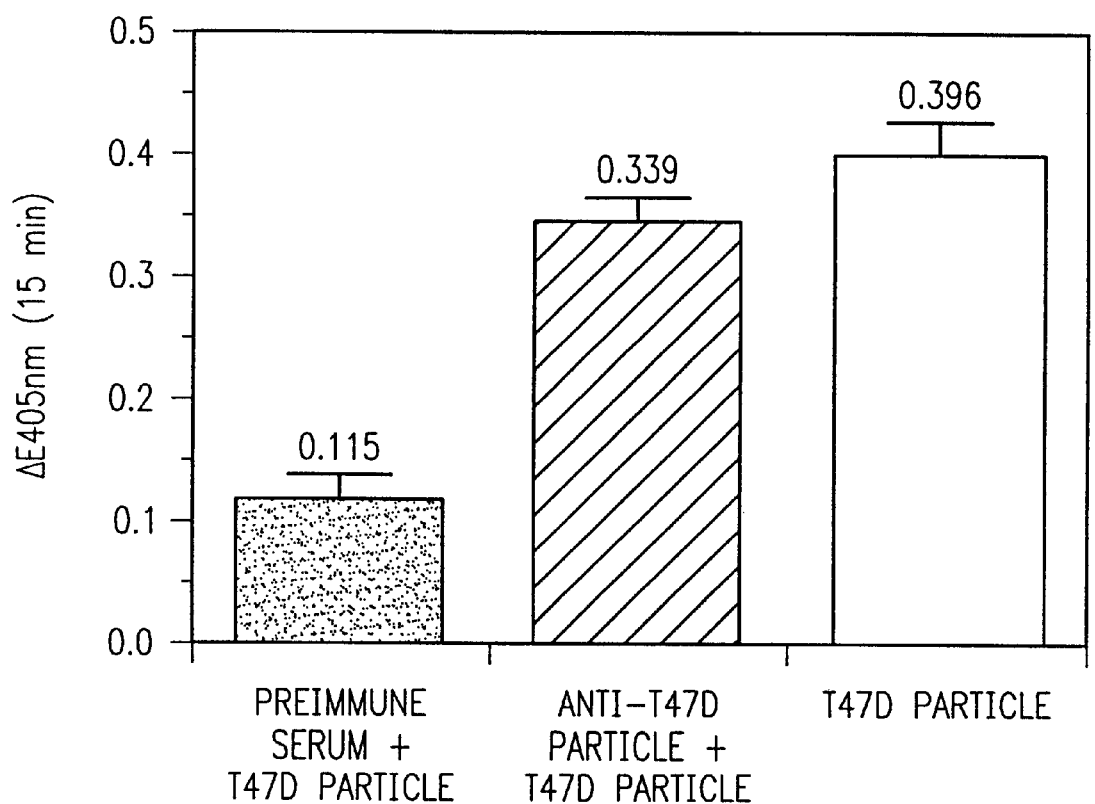

DIRECT AND BIOCHEMICALLY FUNCTIONAL DETECTION PROCESS OF RETROVIRUS IN BIOLOGICAL SAMPLES

I. FIELD OF THE INVENTION

The present invention relates to the detection and identification of retroviruses. More specifically, the invention relates to processes for the direct detection of retroviruses in biological samples. The processes are characterized by the structure-specific extraction of retrovirus particles and a subsequent analysis and detection of retrovirus-specific enzymatic reactions. The processes of the invention have broad application in the diagnosis of retroviral infection and virological research.

II. BACKGROUND

Presently, the routine detection of retroviruses in biological samples is only made indirectly by structure-specific (i.e., non-functional) analysis, namely via the detection of viral-specific antibodies and/or individual components (antigens, RNA proviral DNA). Examples of such detection methods are anti-HIV antibody tests, HIV-p24 antigen tests, and HIV-PCR detection test. Holodniy et al., 1991, *J. Infect. Dis.* 163:862–866; Henrard et al, 1992, *AIDS Res. Hum. Retrovir.* 8:47–52. This type of analysis is based on a structure-specific molecular interaction between antibody and antigen or PCR primer and proviral DNA. Since it is not testing for viral function, it does not establish the presence of biological intact and functional retroviral particles. Furthermore, this type of analysis does not detect all stages of a viral infection, e.g., the phase in which the infection has already taken place, but antibodies have not yet been generated. These factors can cause both false positive or false negative results.

Accordingly, there is a need for the direct and also functional detection of retroviruses in biological samples. This need is further underscored by the medical and sociopolitical significance of retroviruses, presently lead by the greatest medical challenge, AIDS, and by an observable increasing tendency and role of retroviruses in animal and human disease (leukemia, auto-immune diseases, cancer, etc.). In addition, the transmissibility of retroviruses by infection poses a serious challenge on the transfusion and transplantation medicine, calling for reliable detection of viral contamination, both for lymph, saliva, sperm or blood samples, and for organs, skin, bone marrow, etc., to be transplanted. The same problem of viral contamination and infection also applies to the use of pharmaceutical preparations and other pharmaceutical/biotechnological or genetechnological preparations with biological origin for treating diseases in human beings and animals, as well as in basic medical research. A prerequisite for a solution to the above-mentioned problems is the direct detection of functional retroviruses by means of a simple, reliable and sensitive method.

Prior to the present invention, the direct and biologically functional detection of retroviruses was only possible in individual cases. It was labor and time intensive, involving the infection of cells using purified virus preparations or cell culture supernatants. Quantitative, simple and reliable routine methods have not existed prior to this invention. This is due to the complex composition of biological samples (blood, organ extracts, etc.) which contain proteins, enzymes, vitamins, lipids, sugars and various inhibitors. They hinder or render impossible the direct and functional detection of retrovirus.

The process of the present invention provides for the routine, direct and biochemically functional detection of retrovirus in biological samples.

III. SUMMARY OF THE INVENTION

The present invention relates to the detection and identification of retroviruses. In particular, the invention relates to processes for the direct detection of retroviruses in biological samples.

More specifically, the retrovirus particles are extracted based on their structure-specific characteristics. Subsequently, the presence of functional retrovirus is identified by analysis and detection retrovirus-specific functional reactions. For example, retrovirus-specific ligands may be employed for extraction, and retrovirus-specific enzymes may be employed for the subsequent functional analysis.

The processes of the invention have broad application in diagnosis of retroviral infection and virological research.

IV. BRIEF DESCRIPTION OF THE FIGURES

FIG. 1 depicts the biochemically functional detection of reverse transcriptase of T47D particles which were immunologically extracted from culture media with T47D specific antibodies.

V. DESCRIPTION OF THE INVENTION

A. The Process of Direct and Biochemically Functional Detection of Retroviruses In Biological Samples The disclosed process for the direct and biochemically functional detection of retroviruses in biological samples consists of three steps: (A) an extraction step; (B) a reaction step; and (C) a detection step.

1. The Extraction Step

The extraction of retroviral particles from a sample is based on the selective binding of retroviral surface molecules to ligands having specificity for such retroviral surface molecules, which are, in turn, bound to a solid carrier material. As a result, the retroviral particles are immobilized in a carrier-ligand-virus complex and can be extracted selectively from the complex sample mixture. A selective extraction of retroviral membrane-free virus-core particles and intracisternal particles by means of core-specific ligands offers itself for the detection of retroviruses in tissue extracts. The selectivity of the extractions is based on the choice of a ligand selectively binding to a surface molecule specific for the respective retrovirus species. Viral-specific ligands may be: a) antibodies (monoclonal or polyclonal) which are directed against antigenic surface epitopes of a retrovirus, b) receptors, receptor supramolecular complexes or receptor epitopes (as natural, synthetic or recombinant protein and peptide, soluble or membrane-bound in liposomes, membrane preparations/fractions or cells) which are used by the virus to infect and penetrate, a cell, c) anti-receptor-idiotypical antibodies (monoclonal or polyclonal) which imitate binding structures of the viral-specific receptors or d) complement proteins/peptides which bind soluble virus-antibody immunity complexes existing in the sample via Ig-Fc regions. As an alternative, a combination of several of the above-mentioned ligands can also be employed for the selective binding of retroviral particles.

Since the extraction step is based on a purely structural interaction, it does not make a distinction between whole virus particles and viral surface components, e.g., glycoproteins. Therefore, the carrier-ligand-virus complex is tested in a subsequent functional enzymatic reaction step which is specific to retroviruses and can only be carried out by an intact virus particle but not by individual virus components.

2. The Reaction Step

The reaction step is based on a retrovirus-specific enzymatic reaction which imitates in vivo reactions in a retrovirus-infected cell and can be carried out by several specific viral enzymes: reverse transcriptase, RNAse H, integrase, protease and others. The endogenous reverse transcription is a complex process in which several viral components are involved, namely reverse transcriptase (RT) for transcribing the viral RNA (vRNA) to complementary DNA (cDNA), using viral transfer RNA (tRNA) functioning as a primer and exogenously added deoxy-nucleotide-triphosphate (dNTPs). As an alternative to the above-mentioned endogenous reaction, exogenous primers (carrier-bound or unbound), e.g., oligodeoxy-guanosine-triphosphate (oligo-dG) or oligo-deoxy-thymidine-triphosphate (oligo-dT) and exogenous templates e.g., poly-cytosin-triphosphate (poly-rC) or poly-adenosine-triphosphate (30 µg/ml), can be added to the reverse transcription reaction to identify the biochemical functionality of the reverse transcriptase enzyme. The reverse transcription reaction of the carrier-ligand-virus complex does not have to be stopped when the detection is based on the immobilization of the newly synthesized cDNA (e.g., labeling with biotin, Br-digoxigenin, FITC). In the case of accurate kinetic investigations which require a reaction stop, the reaction can be terminated on account of the immobilization of the ligand-virus complex by replacing the lysis-reaction mixture with stopper mixture which does not contain any dNTPs. This termination step also has the advantage that the labeled educts (dNTPs) can easily be separated from the products, thus increasing the test susceptibility significant]y. By a subsequent complete lysis of the virus, the newly synthesized cDNA is released for detection. The incorporation of dNTPs and the synthesis of cDNA is direct evidence for the biochemical functionality of the retrovirus and shows the simultaneous presence of functional viral components (vRNA, tRNA and RT) in the sample.

In addition, the reverse transcription reaction can be continued, namely via synthesis of the second cDNA strand and double-stranded cDNA (by means of the enzyme's DNA polymerase activity) and the subsequent integration thereof into a plasmid (by means of retrovirus-specific integrase activity). The integrated dsDNA is detected in a subsequent detection step like the previously synthesized cDNA.

3. The Detection Step

In the detection step, the enzymatically synthesized reaction products are quantitatively measured by means of radioactive or non-radioactive labeling using optical, fluorescent or luminescent processes.

The cDNA synthesized by the reverse transcriptase is labeled during the enzymatic synthesis by the incorporation of Br-, biotin-, fluorescent- ordigoxigenin-labeled dUTP (deoxy-uridine-triphosphate). The labeled cDNA is immobilized by means of absorption with specific ligands bound to a solid carrier (streptavidin, antibodies, oligonucleotides) and separated from the educts, then quantitatively measured by means of further labeling-specific antibodies which are coupled with an indicator enzyme (peroxidase, alkaline phosphatase) and corresponding enzyme substrates. The measurement can be made photometrically and be evaluated quantitatively.

In the case of radioactive or fluorescent labeling of the educts, the labeled educts can be separated from the immobilized ligand-virus complex as described for the above-described reaction stop and measured quantitatively directly by means of scintillation or fluorescent emission. As an alternative, the labeled cDNA can be precipitated, separated from the educts by means of absorption on filters and then measured.

B. Advantages of the Process

For the first time, the described process enables the routine, direct and functional detection of retrovirus in biological samples. As compared to formerly existing detection methods it has the following advantages:

(a) With comparably high sensitivity, retroviral particles are detected specifically and directly in biological material by means of identifying several retroviral components (antigens, enzymes and nucleic acids).

(b) The detection is not only made structurally (in the extraction step) using retrovirus-specific ligands, but also in biochemically functional fashion by detecting the presence of retrovirus-specific enzymes (reverse transcriptase, RNAse H, integrase, protease) imitating the in vivo reaction thus ensuring an improved specificity of the process.

(c) The detection is made quantitatively.

(d) The process can be carried out quickly, without involving complicated technology, is applicable routinely—since it is adapted to microtiter format,—and is inexpensive.

(e) The process can be applied universally to all retrovirus species by using ligands having the appropriate specificity.

C. Fields of Application

The potential applications of the process can be divided in four major fields.

1. Medical Diagnosis Of Diseases Related To Retroviral Infection

In one embodiment, the field of application of the processes disclosed herein relates to the medical diagnosis and follow-up in the treatment of retrovirus-dependent diseases, e.g., AIDS and leukemia in humans. The same application also applies to retrovirus-dependent diseases in animals. The potential customers are clinics and hospitals as well as clinical laboratories and laboratory associations.

2. Virological Research

In a second embodiment, the field of application of the present processes relates to virological research and development, conducted, for example, in laboratories of universities, large-scale research institutes and industry, where experimental models are researched to develop possible antiviral treatments, vaccines, etc. For those studies, the direct detection of retroviruses (in vitro models, animal models, etc.) is absolutely necessary.

3. Transplantation and Transfusion Medicine

In still another embodiment, the present processes are applied in the entire transplantation and transfusion medicine and the donor banks of blood, organs, bone marrow, sperms, etc. The detection of retrovirus contamination of the above-mentioned donor materials is extremely important to prevent spreading and infection by transplantation or donation.

4. Quality Control of Biological Pharmaceutical Preparations and Biotechnological Products A fourth field of application relates to the quality control of biological and pharmaceutical preparations, e.g., blood derivatives and coagulation preparations, biotechnological products, e.g., immunoglobulins, therapeutic enzymes, insulin, fetal sera, etc., biological cosmetics and certain foodstuff prepared by genetic engineering which have to be investigated as to retroviral contamination to prevent the possible transmission thereof.

VI. EXAMPLE

In order to optimize the process, retroviral T47D particles were used as the model virus, which have the following retrovirus- typical properties: lipid membrane envelope, glycoproteins, reverse transcriptase, genomic RNA, endogenous cDNA synthesis and an endogenous distribution within the human genome. Faff et al., 1992, *J. Gen. Virol.* 73:1087–1097.

A. Extraction

Polyclonal antibodies (10 µg/ml) which are directed against the T47D particles were bound overnight in a coating buffer (50 mM carbonate buffer, pH 9.6) to a microtiter plate. Subsequently, the still free binding sites of the plate were blocked with 1% BSA in coating buffer at room temperature for 60 min, and then the supernatant of unbound material was washed with washing buffer (300 mosmoles phosphate-buffer-saline (PBS) or Tris/HCl, pH 7.4, NaCl). Pre-immune serum was used as negative control, which did not contain any T47D particle-specific antibodies but as incubated with T47D particles. The T47D particle-containing sample was used as positive control, which was not preadsorbed and immobilized with specific antibodies.

B. Reaction

The microtiter plate coated with antibodies was then incubated with 100 µl/well sample 4° C. overnight, consisting of: RPMI medium, 10% fetal calf serum and 10 µg of purified T47D particles. Then, the carrier-ligand-virus complex of unbound material was washed in washing buffer, lysed in a lysis-reaction mixture buffer and incubated in the presence of a dNTP mixture at 42° C. for 60 min. The lysis-reaction mixture buffer had the following composition: 0.3% NP40, 50 mM Tris/HCl, pH 7.8, 40 mM KCl, 5mM $MgCl_2$, 2 mM DTT, 2 mM EDTA and in each case 30 µM dATP, dCTP, dGTP and dTTP+dUPT-biotin+dUTP-digoxigenin. The incorporation of the dNTPs and the synthesis of cDNA, was measured subsequently.

C. Detection

The lysis-reaction mixture was transferred to streptavidin-coated microtiter plates and incubated for immobilizing the biotin- and digoxigenin-labeled cDNA at 37° C. for 1 hour. Having washed the unbound material, the immobilized cDNA was incubated with peroxidase-coupled anti-digoxigenin antibodies (1 hour at 37° C.), washed and then incubated with the peroxidase substrate ABTS (available from Böhringer Mannheim, Mannheim, Germany). The color development was measured by means of photometry at 405 nm after 5 min (and 490 nm as reference). Eberle and Seible, 1992, *J. Virol. Meth.* 40:347–356.

The results are illustrated in FIG. 1. T47D particles are extracted immunologically by means of specific antibodies from the cell culture medium and then biochemically functionally detected by means of endogenous reverse transcription.

What is claimed is:

1. A process for detecting biochemically functional retrovirus in a biological sample, comprising extracting retrovirus particles under physiological conditions using a structure-specific ligand binding to virus surface antigens under conditions that do not destruct retroviral enzymatic functions, followed by a step of measuring the functional activity of a retrovirus-specific enzyme.

2. The process of claim 1, wherein said structure-specific ligand is an antibody, a receptor, a lectin, a proteins, or a peptide, and wherein said retrovirus-specific enzyme is selected from the group consisting of reverse transcriptase, RNAse H, integrase and protease, and said retrovirus-specific enzyme is identified by analysis of a labeled newly synthesized reaction product using radioactive, photometric methods, luminescent processes, or fluorescent processes, said product being selected from the group consisting of cDNA, DNA samples, oligonucleotides, peptides and proteins.

3. The process of claim 2, wherein said structure-specific ligand is bound covalently or noncovalently, directly or by means of a spacer to a solid carrier, said solid carrier being selected from the group consisting of microtiter plates, carrier probes, magnetic carrier spheres and non-magnetic carrier spheres.

4. The process of claim 2, wherein said structure-specific ligand is one or a combination of:
   (a) a viral-specific antibody directed against an antigenic surface or core epitope of the corresponding retrovirus;
   b) a viral-specific receptor, receptor complex or receptor component which is used by the virus to infect a cell, to penetrate a cell or to infect and penetrate a cell;
   c) an anti-receptor-idiotypical antibody which imitates a virus-binding epitope of the corresponding retroviral receptor; or
   d) a complement protein or peptide which binds soluble retroviral antibody immune complexes via the Fc region of the said retroviral antibody.

5. The process of claim 5, wherein said structure-specific ligand is a natural, a synthetic or a recombinant protein or peptide, wherein said protein or peptide is present in soluble form or membrane-bound in liposomes, membrane preparations, membrane fractions or whole cells.

6. The process of claims 5, wherein said structure-specific ligand is immobilized to a carrier and incubated with a sample containing a retrovirus at 4° C. overnight, followed by a wash of complexes formed between said ligand, said retrovirus and said carrier in 300 mosmoles phosphate buffer or Tris/HCl, pH 7.4.

7. The process of claim 6 wherein said complexes formed between said structure-specific ligand, retrovirus and carrier are lysed and tested as to enzymatic activity of reverse transcriptase.

8. The process of claim 6, wherein said complexes formed between said structure-specific ligand, retrovirus and carrier are lysed and tested as to enzymatic activity of one or more enzymes selected from the group consisting of retrovirus-specific enzymes and reverse transcriptase, RNAse H, integrase and protease.

9. The process of claims 8, wherein said lysis is performed using a buffer comprising 10–50 mM Tris/HCl pH 7.8, 2 mM PMSF, 2 mM DTT, 0.1–1% (v/v) NP40, 2 mM EDTA.

10. The process of claim 9, wherein said buffer further contains a mixture of deoxy-nucleotide-triphosphates, said deoxy-nucleotide-triphosphates selected from the group consisting of dATP, dGTP, dCTP and dTTP, and dUTP said dUTP containing a label selected from the group consisting of Br, fluorescent, biotin digoxigenin label, said label being used to quantitatively measure the nucleotide incorporation into the newly synthesized cDNA by means of endogenous reverse transcription.

11. The process of claim 10, wherein said buffer further comprises primers and templates, said primers being selected from the group consisting of carrier-bound primers and unbound primers, and said templates being selected from the group consisting of poly-cytosin-triphosphate and poly-adenosine-triphosphate.

12. The process of claim 11, wherein said buffer comprises 50 mM Tris/HCl, pH 7.8, 40–80 mM KCl, 5–10 mM MgCl$_2$, 2 mM PMSF, 2 mM DTT, 0.1–1% (v/v) NP40, 2 mM EDTA, 30–500 µM of each of dATP, dCTP, dGTP and dTTP, and dUTP, wherein said dUTP has a label selected from the group consisting of Br, biotin, digoxigenin with fluorescent means, and radioactively labeled deoxynucleotide-triphosphate.

13. The process of claim 12, wherein said buffer is exchanged with a stopper mixture said stopper mixture comprising 50–100 mM Tris/HCl, pH 7.8, 40–80 mM KCl, 0.1% (v/v) NP40, 5 mM EDTA.

14. The process of claim 13, wherein
  a) a retrovirus is lysed by means of a lysis buffer at room temperature for 15 min, said lysis buffer comprising 1% NP40, 10 mM Tris/HCl, pH 7.8, 2 mM EDTA; and
  b) newly synthesized cDNA is released for detection.

15. The process of claim 8, wherein said labeled newly synthesized reaction products of said retrovirus-specific enzymes including said reverse transcriptase are detected by means selected from the group consisting of fluorescence, photometry, luminescence and scintillation means.

16. The process of claim 15, wherein
  a) said reaction products are carrier-immobilized, labeled and separated from soluble labeled molecules by washing off said soluble labeled molecules; and
  b) said reaction products are measured quantitatively either directly by means of fluorescence, said fluorescence being detected through emission or scintillation, or by means of measuring photometrically or luminometrically substrates of enzymes, said enzymes being bound to ligands, said ligands binding to said reaction products.

17. The process of claim 15, wherein said reaction products are labeled by labeling means selected from the group consisting of Br, biotin, digoxigenin and fluorescent means, and
  a) immobilized by means of specific carrier-bound ligands, which ligands are selected from the group consisting of antibodies, streptavidin and oligonucleotides;
  b) separated from Br, biotin, digoxigenin and fluorescent means; and
  c) measured quantitatively in photometric or luminometric fashion by means of ligand-bound indicator enzymes and the corresponding substrates, wherein said ligand- bound indicator enzymes are selected from the group consisting of alkaline phosphatase and peroxidase.

* * * * *